United States Patent
Kim et al.

(10) Patent No.: US 9,683,987 B2
(45) Date of Patent: Jun. 20, 2017

(54) GASTRIC CANCER CELL LINE DERIVED FROM MURINE GASTRIC ADENOCARCINOMA LACKING P53 AND E-CADHERIN AND USE THEREOF

(71) Applicant: National Cancer Center, Goyang-si (KR)

(72) Inventors: Hark Kyun Kim, Goyang-si (KR); Jun Won Park, Seoul (KR)

(73) Assignee: National Cancer Center, Goyang-si (KR)

( * ) Notice: Subject to any disclaimer, the term of this patent is extended or adjusted under 35 U.S.C. 154(b) by 0 days.

(21) Appl. No.: 15/011,124

(22) Filed: Jan. 29, 2016

(65) Prior Publication Data

US 2016/0223523 A1 Aug. 4, 2016

(30) Foreign Application Priority Data

Jan. 30, 2015 (KR) ........................ 10-2015-0015192

(51) Int. Cl.
- *C12Q 1/68* (2006.01)
- *G01N 33/50* (2006.01)
- *C12N 5/09* (2010.01)
- *G01N 33/574* (2006.01)

(52) U.S. Cl.
CPC ....... *G01N 33/5011* (2013.01); *C12N 5/0693* (2013.01); *C12Q 1/68* (2013.01); *G01N 33/5044* (2013.01); *G01N 33/57446* (2013.01)

(58) Field of Classification Search
None
See application file for complete search history.

(56) References Cited

FOREIGN PATENT DOCUMENTS

KR 101456627 B1 11/2014

OTHER PUBLICATIONS

Desoize et al., "Multicellular resistance: a paradigm for clinical resistance?" *Critical Reviews in Oncology/Hematology* 36:193-207, 2000.
Park et al., "Cooperativity of E-cadherin and Smad4 Loss to Promote Diffuse-Type Gastric Adenocarcinoma and Metastasis," *Mol Cancer Res* 12:1088-1099, 2014.
Park et al., "Establishment and characterization of metastatic gastric cancer cell lines from murine gastric adenocarcinoma lacking Smad4, p53, and E-cadherin," Mol Carcinog., 8 pages, 2014.
Parkin et al., "Estimates of the worldwide incidence of 25 major cancers in 1990," *Int. J. Cancer* 80:827-841, 1999.
Shan et al., "Establishment of an Orthotopic Transplantable Gastric Cancer Animal Model for Studying the Immunological Effects of New Cancer Therapeutic Modules," *Molecular Carcinogenesis* 50:739-750, 2011.
Von Hoff, "There Are No Bad Anticancer Agents, Only Bad Clinical Trial Designs—Twenty-first Richard and Hinda Rosenthal Foundation Award Lecture," *Clinical Cancer Research* 4:1079-1086, 1998.

*Primary Examiner* — Jim Ketter
(74) *Attorney, Agent, or Firm* — Seed IP Law Group LLP

(57) ABSTRACT

Provided is a gastric cancer cell line derived from a mouse deficient in E-cadherin and p53, and a use thereof. The E-cadherin- and p53-deficient, murine-derived gastric cancer cell line of the present invention was confirmed to have histopathological characteristics similar to those of human gastric cancer, have an epithelial mesenchymal transition (EMT) phenotype and an activated β-catenin pathway, and promote cancer growth in vivo due to potential of carcinogenesis, and thus the gastric cancer cell line of the present invention can be effectively used for the evaluation of the activity of new anticancer drugs and the development of metastasis inhibitors.

6 Claims, 9 Drawing Sheets

GASTRIC CANCER CELL LINE DERIVED FROM MURINE GASTRIC ADENOCARCINOMA LACKING P53 AND E-CADHERIN AND USE THEREOF

CROSS-REFERENCE TO RELATED APPLICATIONS

This U.S. non-provisional patent application claims priority under 35 U.S.C. §119 of Korean Patent Application No. 10-2015-0015192, filed on Jan. 30, 2015, the entire contents of which are hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690196_403_SEQUENCE_LISTING.txt. The text file is 4.6 KB, was created on Jan. 28, 2016, and is being submitted electronically via EFS-Web.

BACKGROUND OF THE INVENTION

The present invention disclosed herein relates to a gastric cancer cell line derived from a mouse deficient in E-cadherin and p53, and a use thereof, and more specifically, to a murine gastric cancer cell line NCC-S3/NCC-S3M, which shows a phenotype very similar to that of human gastric cancer due to the deficiency in E-cadherin and p53, which are the genes where mutations are most frequently observed in human diffuse-type gastric cancer, an immunotherapy using the gastric cancer cell line, and a method of evaluating the efficacies of therapeutic agents for treating gastric cancer and/or evaluating toxicities of the same.

SUMMARY OF THE INVENTION

The core of the preclinical study for the development of novel anticancer drugs or anticancer therapies lies in accurate and rapid evaluation of their anticancer activities. For the development of novel anticancer drugs or anticancer therapies, an in vitro experimental system is more economical and excellent in terms of cost and promptness compared to that of an in vivo experimental system. However, the validity of efficacy evaluation in the in vitro experimental system relies on whether the in vitro experimental system can verify the efficacies with experimental significance by sufficiently representing the situation of the in vivo system. Until recently, about 90% of candidate anticancer materials which had entered into preclinical studies through the preclinical development stage have failed in the final development, and this implies that the compounds having the potential of clinical efficacies have not been discovered due to the absence of an appropriate experimental system (von Hoff D. D., Clin Cancer Res., 4:1079, 1998).

Examples of the in vitro chemosensitivity assays that have been widely used until now may include clonogenic assay, dye exclusion assay, tetrazolium salt 3-(4,5-dimethylthiazol-2-yl)-2,5-diphenyl tetrazolium bromide assay (MTT assay), sulforhodamine B assay (SRB assay), etc. The above methods may be of significance as the primary screening system in the development of new drugs which requires high-throughput, however, their conditions differ greatly from those in human solid cancer thus making it difficult to predict the response rate to solid cancer. In the case of solid cancer, the low response rate to anticancer chemotherapies has been known to be ascribed to the drug resistance which has been induced by the three-dimensional organization of solid cancer cells and various mechanisms including the intercellular interactions and the interactions between the cells and extracellular matrix (ECM) resulted from a multicellular system, which cause deterioration in invasion into cancer tissues and decrease in concentration within the tissues (Bernard D. et al., Crit Rev Oncol Hematol., 36: 193, 2000).

Meanwhile, gastric cancer is one of the most frequently occurring cancers showing No. 1 death rate (Parkin et al., Int. J. Cancer, 80:827, 1999). In addition, the symptoms of gastric cancer vary a lot from having no pain at all to a severe pain. The symptoms of gastric cancer may not be particularly characterized but they are similar to those of general digestive symptoms. In fact, gastric cancer at its early stage do not accompany any symptoms in general. Even when there is a symptom, it is rather at a negligible level to be felt merely as a slight indigestion or inconvenience in epigastrium thus making most people with gastric cancer ignore and thereby increasing the death rate due to gastric cancer. Therefore, about 90% of the gastric cancer patients die after the gastric cancer becomes worsened into a metastatic cancer rather than dying in the state of the primary culture.

Currently, for the preclinical study of an anticancer agent for gastric cancer, a human gastric cancer cell line is injected into an immunosuppressive mouse (an SCID or nude mouse) for the evaluation of a new anticancer drug. However, the preclinical study using the immunosuppressive mouse has a limitation in that it is not suitable for the method of evaluating the efficacy of immunotherapies and the safety of immunological treatment, and thus there is a need for the development of a gastric cancer cell line model similar to that of human gastric cancer for the development of a metastatic inhibitor of gastric cancer.

However, although orthotopic allograft models (a method of improving reliability and accuracy of efficacy evaluation by providing an environment most similar to that of a given disease, and it can construct a disease model by transplanting a gastric cancer cell into a gastric tissue and thereby develop an animal model similar to that of the clinical study) have an advantage in a physiologically microenvironment in a mouse with immunological competence, they have a limitation in that they are very rare in scientific circles, continue to induce cancer, and are not well defined genetically (Shan Y S, et al., Mol Carcinog., 50:739, 2011).

Under these circumstances, the present inventors endeavored to establish a murine-derived gastric cancer cell line similar to that of human gastric cancer, and selected two gastric cancer cell lines, i.e., NCC-S3 and NCC-S3M, from the gastric adenocarcinoma formed naturally in the orthotopic allograft models established in a mouse with immunological competence, and it was confirmed that the gastric cancer cell lines had phenotypes similar to that of human gastric cancer because of the loss of E-cadherin and p53, which are the genes where mutations are most frequently observed in human diffuse-type gastric cancer, an immunotherapy using the gastric cancer cell line, and it was also confirmed that the NCC-S3M cell line had the phenotype of epithelial mesenchymal transition (EMT) in which the β-catenin pathway was activated, and the NCC-S3M cell line promoted the growth of cancer in vivo due to the potentials on high metastasis and carcinogenesis, thereby completing the present invention.

Being contrived to solve the limitations described above, a first object of the present invention is to provide a gastric cancer cell line derived from a mouse which is deficient in E-cadherin and p53.

A second object of the present invention is to provide a system including a gastric cancer cell line for evaluating drug efficacies or a method for discovering a gene capable of inhibiting metastasis.

To achieve the first object of the present invention, the present invention provides a gastric cancer cell line which is deficient in E-cadherin and p53.

In an exemplary embodiment of the present invention, the gastric cancer cell line may be derived from a mouse.

In another exemplary embodiment of the present invention, the gastric cancer cell line may include the gastric cancer cell line with Korean Cell Line Bank Accession No. KCLRF-BP-00320 or the gastric cancer cell line with Korean Cell Line Bank Accession No. KCLRF-BP-00321.

In still another exemplary embodiment of the present invention, the gastric cancer cell line may be prepared by isolation from the gastric adenocarcinoma formed naturally in Pdx1-cre, Trp53$^{F/F}$, and Cdh1$^{F/F}$ mice.

In still another exemplary embodiment of the present invention, the gastric cancer cell line with Korean Cell Line Bank Accession No. KCLRF-BP-00321 may be prepared by isolation from the pulmonary metastasis product of heterotopic allografts of the gastric cancer cell line with Korean Cell Line Bank Accession No. KCLRF-BP-00320.

In still another exemplary embodiment of the present invention, the gastric cancer cell line with Korean Cell Line Bank Accession No. KCLRF-BP-00321 may have the phenotype of epithelial mesenchymal transition (EMT), in which vimentin may be overexpressed and the Wnt/β-catenin pathway may be activated.

In order to achieve the second object of the present invention, the present invention provides a method for evaluating the efficacies of candidate therapeutic agents for treating gastric cancer, including: (a) treating at least one type of a gastric cancer cell line selected from the group consisting of the gastric cancer cell line with Korean Cell Line Bank Accession No. KCLRF-BP-00320 and the gastric cancer cell line with Korean Cell Line Bank Accession No. KCLRF-BP-00321 with a candidate therapeutic agent for treating gastric cancer and/or a candidate metastasis inhibitor of gastric cancer; and (b) measuring the level of inhibition of gastric cancer cells in step (a) and/or the level of inhibition of metastasis of gastric cancer cells.

The present invention provides a method for evaluating the safety of an immunotherapy, including: (a) treating at least one type of a gastric cancer cell line selected from the group consisting of the gastric cancer cell line with Korean Cell Line Bank Accession No. KCLRF-BP-00320 and the gastric cancer cell line with Korean Cell Line Bank Accession No. KCLRF-BP-00321 with a candidate therapeutic agent for treating gastric cancer and/or a candidate metastasis inhibitor of gastric cancer; and (b) measuring the safety of immunotherapy on gastric cancer cells in step (a).

ADVANTAGEOUS EFFECTS OF THE INVENTION

The E-cadherin- and p53-deficient, murine-derived gastric cancer cell line of the present invention was confirmed to have histopathological characteristics similar to those of human gastric cancer, have an epithelial mesenchymal transition (EMT) phenotype and an activated β-catenin pathway, and promote cancer growth in vivo due to high metastatic property in an immune-deficient mouse and potential of carcinogenesis in a mouse with immunity, and thus the gastric cancer cell line of the present invention can be effectively used for evaluating the activity of new anticancer drugs and the development of metastasis inhibitors.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Hereinafter, the present invention is described in more details.

As described above, there is a requirement for the development of a gastric cancer cell line model similar to that of human gastric cancer in order to develop a metastatic inhibitor of gastric cancer. Although the orthotopic allograft models in a mouse with immunological competence have an advantage in a physiologically microenvironment in a mouse with immunological competence, they have a limitation in that they are very rare and are not well defined genetically.

The present aims at solving the limitation described above by providing a gastric cancer cell line derived from a mouse deficient in E-cadherin and p53. The gastric cancer cell lines, i.e., NCC-S3 and NCC-S3M, have a phenotype similar to that of human gastric cancer due to the loss of E-cadherin and p53. In particular, the NCC-S3 cell line can be effectively used for the evaluation of anticancer new drugs and the discovery of inhibitors of metastasis, because it has an epithelial mesenchymal transition (EMT) phenotype, the β-catenin pathway is activated, and has high metastatic property in an immune-deficient mouse and high potential of carcinogenesis in a mouse with immunity thus capable of promoting the growth of cancer in vivo.

Therefore, the present invention includes a gastric cancer cell line deficient in E-cadherin and p53.

The gastric cancer cell line may be derived from a mouse.

The gastric cancer cell line includes the gastric cancer cell line with Korean Cell Line Bank Accession No. KCLRF-BP-00320 or the gastric cancer cell line with Korean Cell Line Bank Accession No. KCLRF-BP-00321.

Preferably, the gastric cancer cell line may be prepared by isolating from gastric adenocarcinoma which was formed naturally in Pdx1-cre, Trp53$^{F/F}$, and Cdh1$^{F/F}$ mice.

In an aspect of the present invention, an orthotopic allograft model was established in a mouse having immunological competence in order to isolate a murine-derived gastric cancer cell line, and a gastric cancer cell line was isolated from the gastric adenocarcinoma, which was naturally formed by constructing Pdx1-cre, Trp53$^{F/F}$, and Cdh1$^{F/F}$ mice.

Preferably, the animal model is a rodent, and more preferably a mouse, but is not limited thereto. Furthermore, the animal model is preferably one in which cancer occurs therein, more preferably one in which a gastrointestinal cancer occurs, and most preferably one in which gastric cancer, small bowel cancer, and large bowel cancer. In addition, according to an exemplary embodiment of the present invention, the gastric cancer is preferably has the histopathological characteristics same as those of human diffuse-type gastric cancer, and most preferably, poorly differentiated diffuse-type adenocarcinoma having signet ring cells.

Figure 1:
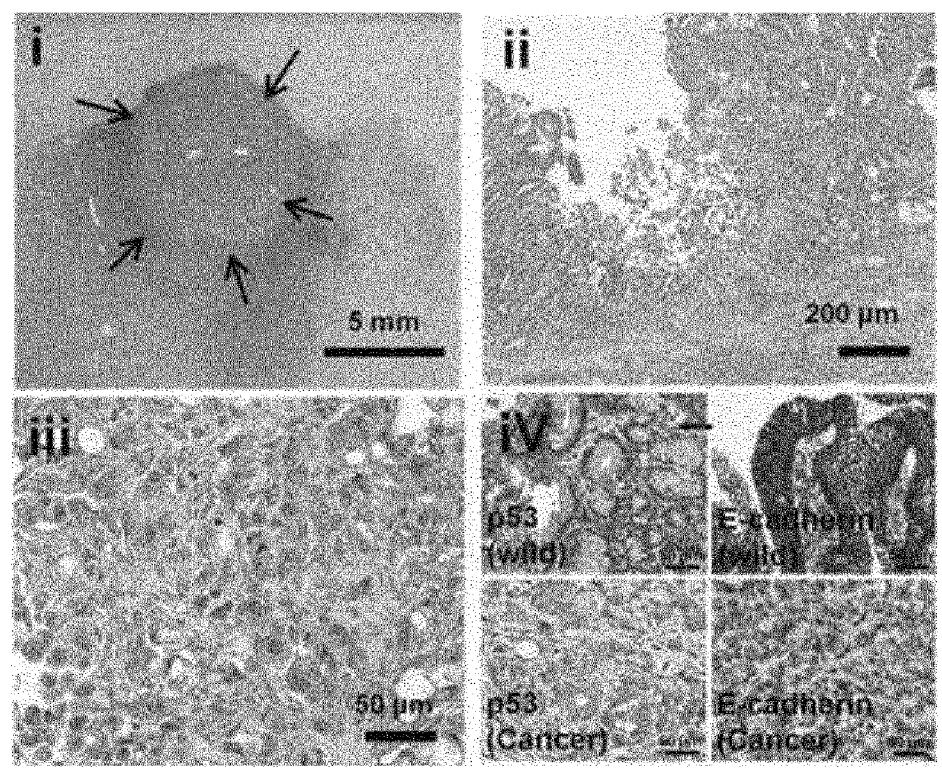
FIG. 1 shows the data of the primary tumors formed in Pdx1-Cre, Trp53$^{F/F}$, and Cdh1$^{F/F}$ mice, and the tumor tissues observed histologically, in which i) shows tumor tissues observed by the naked eye (Gross findings), ii) and iii) show the images under the microscopic finding of the tumor tissues, and iv) shows an image of the immunohistologically-observed expressions of p53 and E-cadherin, which are expressed in normal tissues and tumor tissues, and the arrows indicate the boundaries of tumors.

FIG. 1 shows the data of the primary tumors formed in Pdx1-Cre, Trp53$^{F/F}$, and Cdh1$^{F/F}$ mice and the tumor tissues observed histologically, and the tumors were confirmed to be similar to the human diffuse-type adenocarcinoma, and when the expressions of p53 and E-cadherin, which are expressed in normal tissues and tumor tissues, were observed histologically (iv of FIG. 1), it was confirmed that the E-cadherin and p53 proteins were not expressed in the primary tumor tissues formed in the Pdx1-Cre, Trp53$^{F/F}$, and Cdh1$^{F/F}$ mice.

In an exemplary embodiment of the present invention, cells were isolated from the gastric adenocarcinoma tissues of the Pdx1-Cre, Trp53$^{F/F}$, and Cdh1$^{F/F}$ mice and cultured, and the gastric cancer cell line deficient in E-cadherin and p53 was isolated and designated as NCC-S3.

Figure 2A:
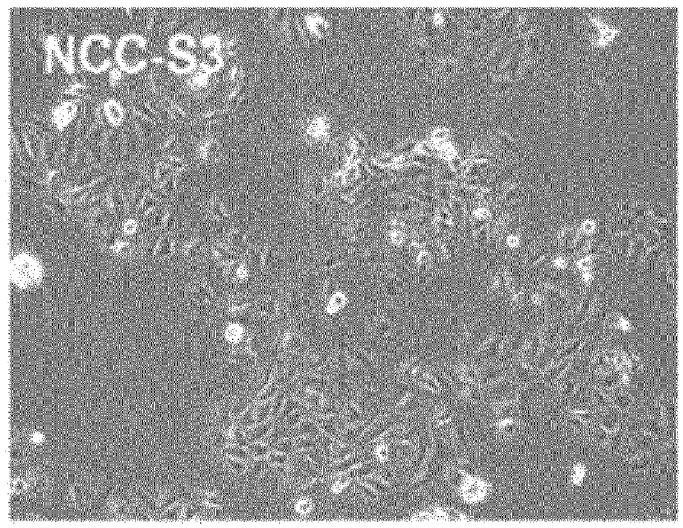
FIGS. 2A and 2B show the images of in vitro cell morphology of NCC-S3 (FIG. 2A) and NCC-S3M (FIG. 2B), respectively, which are gastric cancer cell lines derived from the gastric adenocarcinoma naturally formed in an orthotopic transplantation model (×100).

FIG. 2A shows the cell morphology of the NCC-S3 isolated from the above observed when they were cultured in a cell culture container, and it was observed that the NCC-S3 cell line showed the shape of epithelial cells.

Figure 3A:
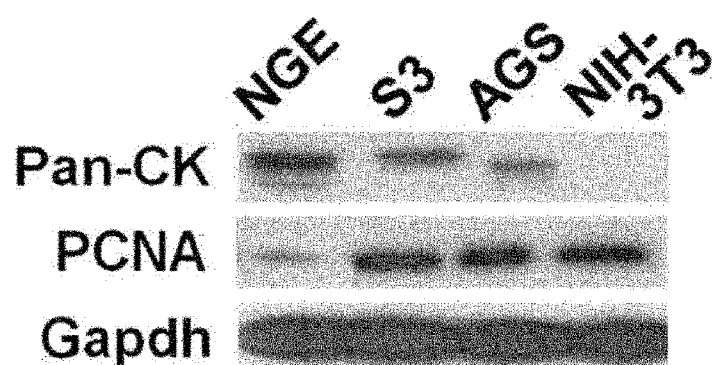
FIGS. 3A and 3B show the data illustrating the expression levels of pan-cytokeratin and proliferating cell nuclear antigen (PCNA) in NCC-S3 cell line (FIG. 3A) and the expression levels of EGFR, p-Erk, p-Akt, Myc, and cyclin D1 (FIG. 3B), confirmed by western blot analysis (NEG: normal gastric epithelial cells, S3: NCC-S3 cell line, ASG: human gastric cancer cell line, and NIH-3T3: murine embryonic fibroblasts).
Figure 3B:
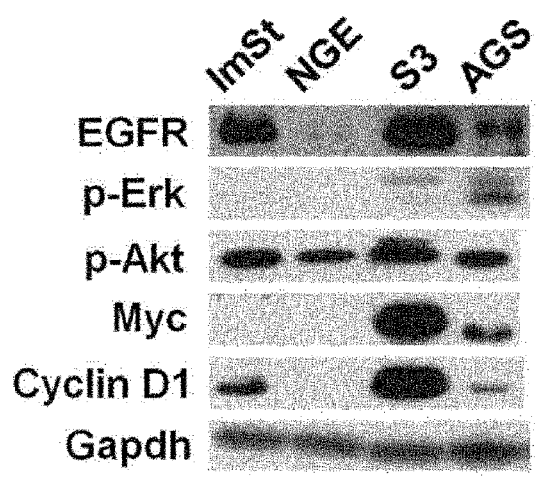

In another exemplary embodiment of the present invention, the expression levels of pan-cytokeratin and proliferating cell nuclear antigen (PCNA) (FIG. 3A) and the expression levels of EGFR, p-Erk, p-Akt, Myc, and cyclin D1(FIG. 3B) were measured by western blot analysis, in order to characterize the NCC-S3 cell line isolated in Example 2 and confirm whether the NCC-S3 cell line shows similarities to those of human gastric cancer cell line. As a result, as shown in FIGS. 3A and 3B, it was confirmed that AGS, which is the human gastric cancer cell line, has the same characteristics as those of the NCC-S3 cell line isolated in the present invention.

Figure 4:
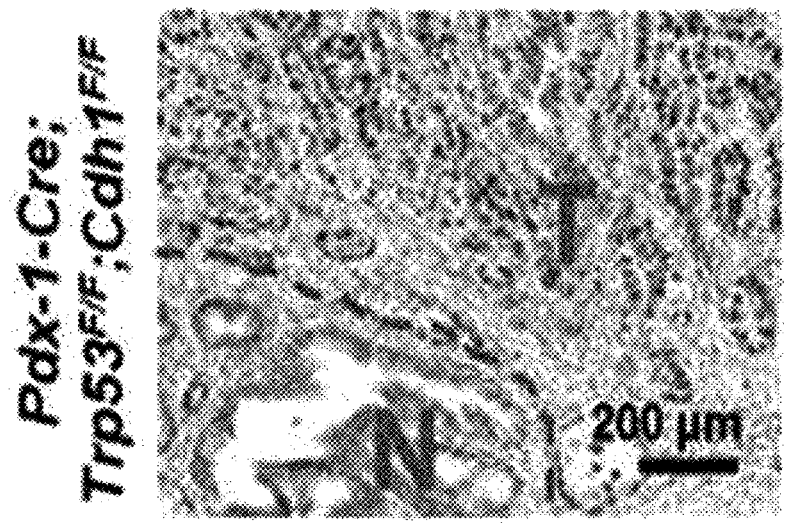
FIG. 4 shows the immunohistologically-observed image of Myc protein in primary tumors derived from Pdx1-Cre, Trp53$^{F/F}$, and Cdh1$^{F/F}$ mice (T: primary tumors, and N: adjacent normal mucosal membrane).

From the result, it can be speculated that the EGFR/MAPK signal is activated in the NCC-S3 cell line isolated in the present invention and that the Wnt/β-catenin signal is activated based on the result that Myc and Cyclin D1, which are Wnt target molecules, were overexpressed. Additionally, as shown in FIG. 4, it was confirmed that Myc overexpression was detected in the primary tumor in which the cells were formed.

Figure 5:
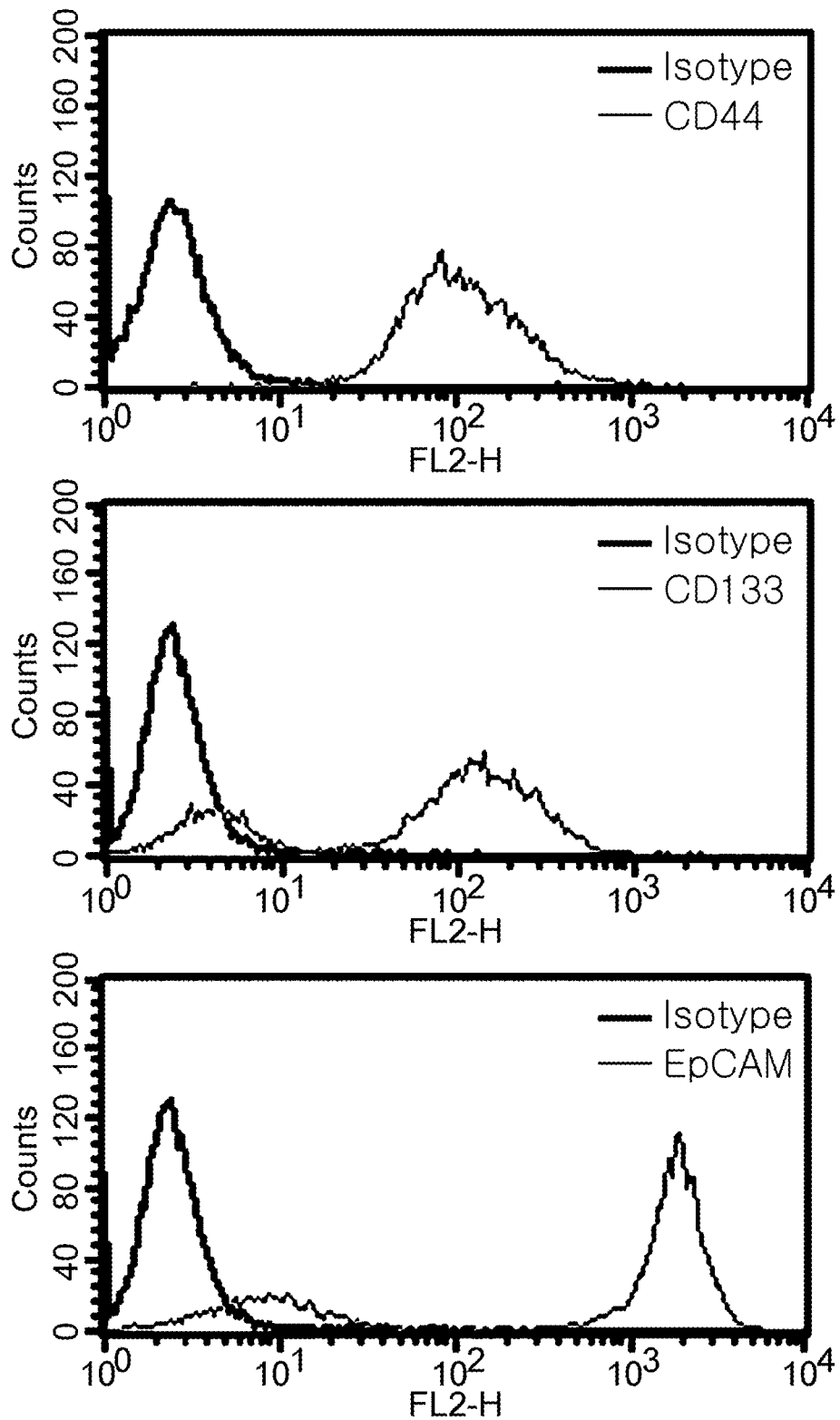
FIG. 5 shows the data illustrating the results of fluorescence activated cell sorter (FACS) in NCC-S3 cell line regarding the CD44, CD133, and EpCAM.

FIG. 5 shows the data illustrating the analysis results of fluorescence activated cell sorter (FACS) in NCC-S3 cell line regarding the CD44, CD133, and EpCAM, and it was confirmed that CD44, CD133, and EpCAM, which are expressed in human gastric cancer, were overexpressed in NCC-S3 cells. That is, it was confirmed that the NCC-S3 cell line established in the present invention is very similar to that of human gastric cancer.

In the present invention, the gastric cancer cell line with Accession No. KCLRF-BP-00321 may be characterized in that it was prepared by isolating from a pulmonary metastasis product of heterotopic allografts of the gastric cancer cell line with Accession No. KCLRF-BP-00320, and the gastric cancer cell line with Accession No. KCLRF-BP-00320 may be such that it has an epithelial mesenchymal transition (EMT) phenotype, vimentin is overexpressed therein, and Wnt/β-catenin pathway is activated.

In an exemplary embodiment of the present invention, in order to establish a cell line with improved capability of metastatic property in addition to the NCC-S3 cell line, the NCC-S3 cell line was transplanted into the subcutaneous tissues of a SCID mouse, and the metastatic lesions observed in pulmonary tissues were cut off, and the NCC-S3M cell line was established in the same method as in Example 2.

Figure 2B:
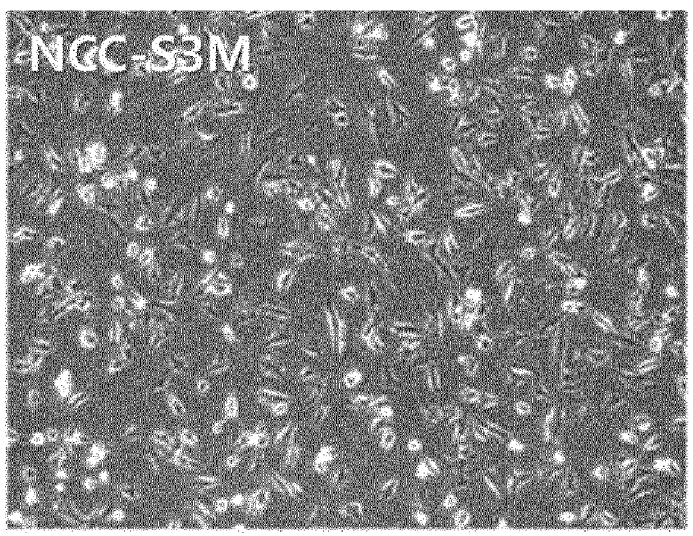

FIG. 2B shows the cell morphology of the NCC-S3M isolated from the above observed when they were cultured in a cell culture container, and it was confirmed that the NCC-S3M cell line has the phenotype of epithelial mesenchymal transition (EMT).

Figure 6:
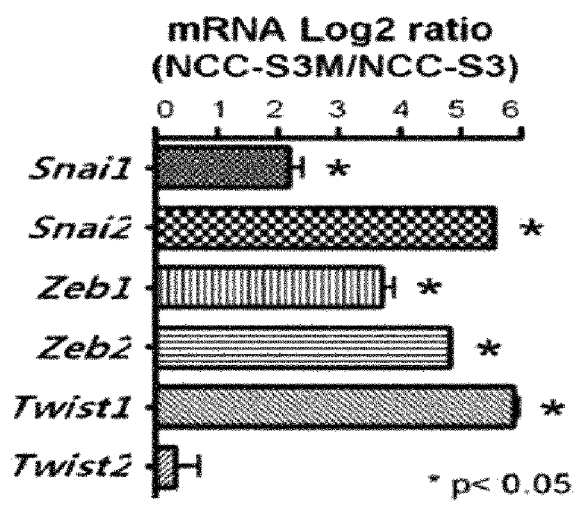
FIG. 6 shows the data comparing the mRNA expression levels of EMT activating transcription factors (Snail 1, Snail 2, Zeb 1, Zeb 2, Twist 1, and Twist 2) of NCC-S3M relative to NCC-S3, for the confirmation of EMT, which is determined to have been contributed to the improvement of metastatic potential of NCC-S3M.

For the confirmation of EMT of NCC-S3M, the mRNA expression levels of Snail 1, Snail 2, Zeb 1, Zeb 2, Twist 1 and Twist 2, which are EMT activating transcription factors, were measured, and the expression level of the increased expression levels of EMT activating transcription factors in NCC-S3M were confirmed (NCC-S3M/NCC-S3). As shown in FIG. 6, NCC-S3M was shown to increase the mRNA expression levels in all of Snail 1, Snail 2, Zeb 1, Zeb 2, Twist 1 and Twist 2, compared to those of NCC-S3, and the metastatic capacity of NCC-S3M was shown to significantly increase compared to that of NCC-S3.

Figure 7:
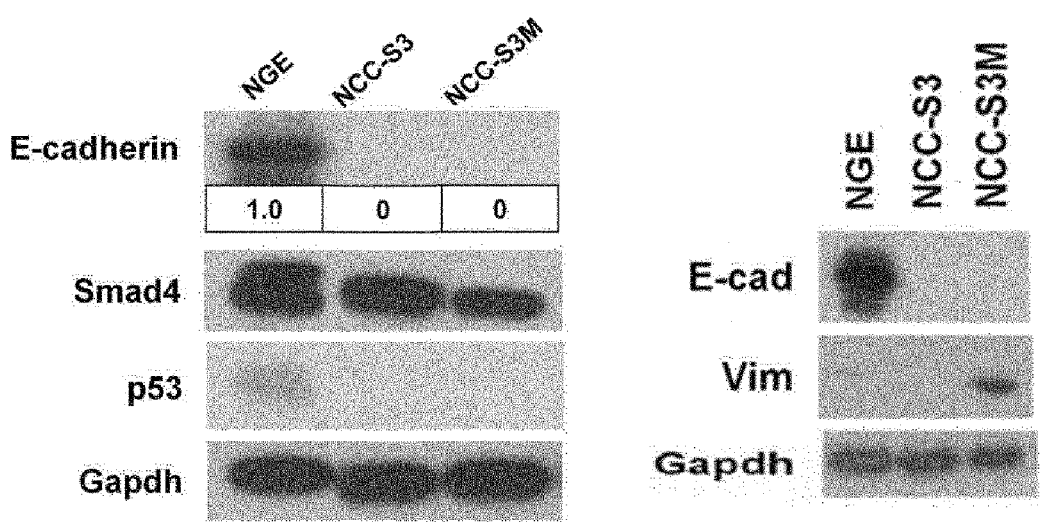
FIG. 7 shows the data illustrating the expression levels of E-cadherin, Smad 3, p53, and vimentin in NCC-S3 and NCC-S3M cell lines, confirmed by western blot analysis.

In addition, in another exemplary embodiment of the present invention, the expression levels of E-cadherin and vimentin in NCC-S3 and NCC-S3M cell lines were confirmed by western blot analysis. As a result, as shown in FIG. 7, both NCC-S3 and NCC-S3M cell lines did not express E-cadherin, whereas vimentin was overexpressed only in NCC-S3M cell line.

From the foregoing, the loss of E-cadherin was known to strongly induce EMT (Park J W, Jong S H, Park D M, Lim N J, Deng C, Kim D Y, Green J E, Kim H K. Loss of E-cadherin and Smad4 cooperate to promote the development and metastasis of diffuse-type gastric adenocarcinoma. *Mol Cancer Res* 2014 August; 12(8):1088-99), and vimentin is an intermediate filament protein specific to mesenchymal cells such as fibroblasts and leukocytes, accelerates invasion function of cancer cells, and is known as a marker for mesenchymal cells.

Figure 8:
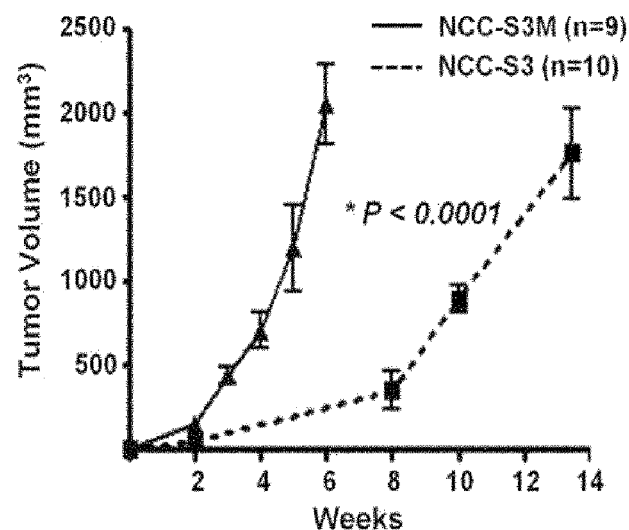
FIG. 8 shows the data illustrating the growth curves of heterotopic allografts of NCC-S3 and NCC-S3M cell lines in an SCID mouse.

FIG. 8 of the present invention shows the data illustrating the growth curves of heterotopic allografts of NCC-S3 and NCC-S3M cell lines in an SCID mouse, and the heterotopic allografts of NCC-S3M showed a faster growth than those of NCC-S3 in an SCID mouse, and it was confirmed that the heterotopic allografts of the NCC-S3M cell line was shown to develop pulmonary metastasis in a continuous fashion when the volume of the primary tumor reached about 2500 mm$^3$ (Table 2).

In contrast, only 10% of the heterotopic allografts of the NCC-S3 cell line developed metastasis, and this suggests that the NCC-S3M cells have improved tumorigenesis and metastatic capacity compared to the NCC-S3 cells.

Furthermore, in order to confirm whether the Wnt/β-catenin signal was substantially activated in the NCC-S3 and NCC-S3M cell lines isolated in the present invention, the expression levels of TCF/LEF1 and β-catenin, the expression levels of Mmp3 and Mmp14 mRNA, and the expression levels of Wnt5a, Wnt10b, and Fzd8 mRNA were measured.

Figure 9:
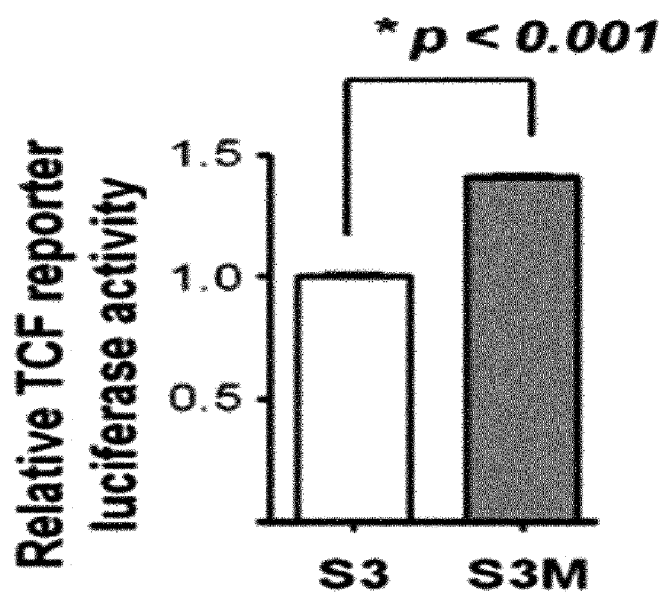
FIG. 9 shows the data illustrating the activities of T-cell factor/lymphoid enhancer factor (Tcf/Lef1) in NCC-S3 and NCC-S3M cell lines measured via reporter assay.

FIG. 9 confirms the activities of T-cell factor/lymphoid enhancer factor (Tcf/Lef1) in NCC-S3 and NCC-S3M cell lines via reporter assay, and the increase of the TCF/LEF1 activity in the NCC-S3M cell line. The "TCF/LEF1" acts as a transcription factor that binds to DNA during a Wnt/β-catenin signaling process. When β-catenin is absent, TCF/LEF1 acts as a transcription inhibitory factor along with co-repressors such as Groucho, CtBP, and HIC-5, whereas when β-catenin is present, TCF/LEF1 acts as a transcription activating factor.

Figure 10:
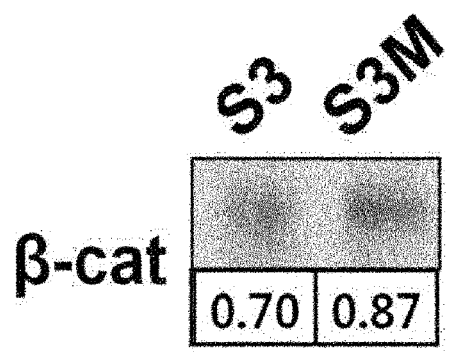
FIG. 10 shows the data illustrating the expression level of β-catenin in NCC-S3 and NCC-S3M cell lines, confirmed by western blot analysis.
Figure 11:
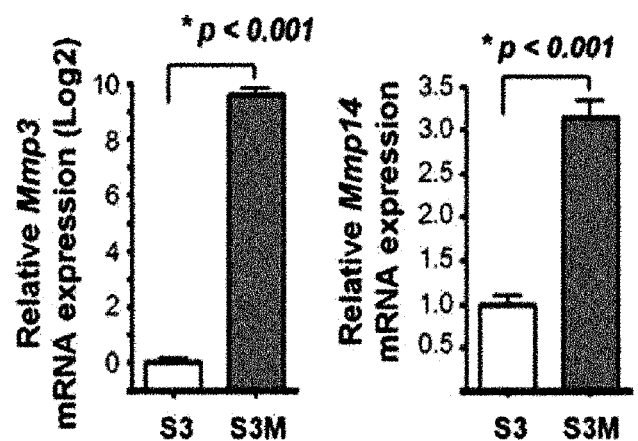
FIG. 11 shows the data illustrating the mRNA expression levels of Mmp3 and Mmp14 measured in NCC-S3 and NCC-S3M cell lines.

FIG. 10 shows the measurement of the presence of expression of β-catenin in NCC-S3 and NCC-S3M cell lines, and both NCC-S3 and NCC-S3M cell lines were confirmed to express β-catenin, and it was confirmed that mRNAs of Mmp3 and Mmp14, which are known as target genes of β-catenin was overexpressed in the NCC-S3M cell line (FIG. 11).

Figure 12:
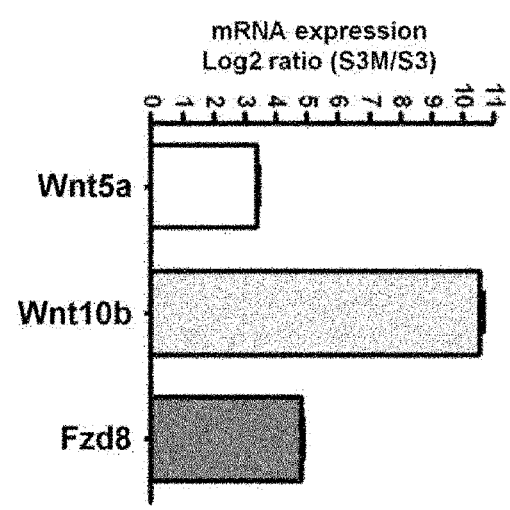
FIG. 12 shows the data illustrating the mRNA expression levels of Wnt5a, Wnt10b, and frizzled-8 (Fzd8) in NCC-S3 and NCC-S3M cell lines.

In addition, as shown in FIG. 12, when the mRNA expression levels of Wnt5a, Wnt10b, and Fzd8 (frizzled-8) in NCC-S3 and NCC-S3M cell lines, it was confirmed that the NCC-S3M cell line showed an increase of mRNA expression of Wnt5a, Wnt10b, and Fzd8 (frizzled-8) compared to those of the NCC-S3 cell line, by a 3-fold, a 10.5-fold, and a 5-fold, respectively.

That is, it was confirmed that the Wnt/β-catenin signaling process was activated indeed in the NCC-S3M cell line established in the present invention, and this suggests that the metastatic phenotype of the NCC-S3M cell line, which is a metastatic cell line, can be partially resulted from EMT through the activation of the β-catenin signaling pathway.

In the present invention, the inventors have established NCC-S3 and NCC-S3M cell lines, which are murine-derived gastric cancer cell lines closely mimicking human gastric cancer and are useful for testing the agents for immunotherapies, and deposited these cell lines to the Korean Cell Line Bank on Jul. 10, 2014 (NCC-S3 cell line: Korean Cell Line Bank Accession No. KCLRF-BP-00320, and NCC-S3M cell line: Korean Cell Line Bank Accession No. KCLRF-BP-00321).

Therefore, the murine-derived gastric cancer cell line of the present invention, which is deficient in E-cadherin and p53, was confirmed to have histopathological characteristics similar to those of human gastric cancer, have an epithelial mesenchymal transition (EMT) phenotype, has an activated β-catenin pathway, promote cancer growth in vivo due to high metastatic property in an immune-deficient mouse and high potential of carcinogenesis in a mouse with immunity, and thus the murine-derived gastric cancer cell line of the present invention can be effectively used for evaluating the activity of new anticancer drugs and the development of metastasis inhibitors.

The present invention provides a method for evaluating the efficacies of candidate therapeutic agents for treating gastric cancer, including: (a) treating at least one type of a gastric cancer cell line selected from the group consisting of the gastric cancer cell line with Korean Cell Line Bank Accession No. KCLRF-BP-00320 and the gastric cancer cell line with Korean Cell Line Bank Accession No. KCLRF-BP-00321 with a candidate therapeutic agent for treating gastric cancer and/or a candidate metastasis inhibitor of gastric cancer; and (b) measuring the level of inhibition of gastric cancer cells in step (a) and/or the level of inhibition of metastasis of gastric cancer.

The present invention also provides a method for evaluating the safety of an immunotherapy, including: (a) treating at least one type of a gastric cancer cell line selected from the group consisting of the gastric cancer cell line with Korean Cell Line Bank Accession No. KCLRF-BP-00320 and the gastric cancer cell line with Korean Cell Line Bank Accession No. KCLRF-BP-00321 with a candidate therapeutic agent for treating gastric cancer and/or a candidate metastasis inhibitor of gastric cancer; and (b) measuring the safety of the immunotherapy on gastric cancer cells in step (a).

Detailed Description of Preferred Embodiments

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

EXAMPLE 1

Construction of a Mouse of Naturally-Occurring Gastric Cancer 1-1 : Construction of a Mouse of Naturally-Occurring Gastric Cancer In the present invention, orthotopic allograft models in a mouse with immunological competence were established for the isolation of a murine-derived gastric cancer cell line, and gastric cancer cell lines were isolated from naturally formed gastric adenocarcinoma by constructing Pdx1-cre, Trp53$^{F/F}$, and Cdh1$^{F/F}$ mice.

The Pdx1-cre, Trp53$^{F/F}$, and Cdh1$^{F/F}$ mice were prepared using the method disclosed previously (Park J W, et al., *Mol Cancer Res.*, 2014), and heterotopic allografts were prepared in mice with immunological competence using the Pdx1-cre-negative, Trp53$^{F/F}$, and Cdh1$^{F/F}$ mice. The severe combined immunodeficiency (SCID) mice were used after purchasing them from Orient Bio Inc. (Korea), and all the animal management and surgery procedures were approved by the Committee of Animal Management and Use of the National Cancer Center (Korea) and the National Cancer Institute (Korea).

1-2 : Observation of Tumors by the Naked Eye and Histopathological Method

For the confirmation of the presence of primary tumors in the Pdx1-cre, Trp53$^{F/F}$, and Cdh1$^{F/F}$ mice constructed in Example 1-1, the mice were autopsied and then observed by the naked eye and histopathological method. Specifically, the mice, which were fasted overnight, were euthanized using isoflurane and then their gastrointestinal tracts were removed immediately thereafter. The stomachs were cut off along the greater curvature using a scissor, and the spread over a filter paper, washed with a cold PBS, and were observed overall.

Then, the tissue samples were obtained from the tissues using a method known in the art, fixed with 10% neutral buffered formalin solution for 24 hours, and the blocks were embedded with paraffin wax. The paraffin blocks were cut off to produce a 5 µm cross section and subjected to Hematoxylin and Eosin (H & E) staining for the histopathological examination. The H & E staining was performed in a conventional method known in the art.

The immunohistochemical analysis was performed using a known method (Park J W, et al., *Mol Cancer Res.*, 2014) and the ABC method (Vectastain Elite ABC kit and Vectastain M.O.M. kit) was used.

In brief, the tissues sliced into a thickness of 5 µm (slides) were dewaxed, rehydrated, and then heated in a 0.01 M citrate buffer (pH 6.0) at 100° C. for 20 minutes for antigen retrieval. Then, the slides were immersed in 3% hydrogen peroxide for 3 minutes for blocking the activity of endogenouse peroxidase, reacted in a blocking reagent contained in the kit for reducing non-specific bindings, and then reacted at room temperature for 20 minutes after treating with diluted primary antibodies.

The primary antibodies used were those antibodies which are specific to p53 (rabbit polyclonal anti p53 antibody (1:100; Santa Cruz, sc-6243) and E-cadherin (rabbit polyclonal anti E-cadherin antibody (1:200; Cell Signaling, #3195).

The resultant was treated with secondary antibodies (biotinylated secondary antibody), which are specific to the primary antibodies, and reacted at room temperature for 30 minutes, and treated with the ABC reagent and reacted at room temperature for 30 minutes. Upon completion of the reaction, the resultant was treated with the ImmPact DAB substrate (Vector Laboratories, SK-4105) for colorimetric detection, and treated with the Mayer's hematoxylin reagent for counterstaining.

For the negative control group, the treatment with the primary antibodies was omitted, and instead the reaction was conducted by treating with a diluent, and each of the positive staining for each marker was stained more distinctively and deeply relative to the background.

As shown in FIG. 1, the tumors isolated from the mice were shown to have a similar shape to that of human diffuse-type gastric adenocarcinoma. As a result of the immunohistological observation of the expression of p53 and E-cadherin, which are expressed in normal tissues and the above tumor tissues (iv of FIG. 1), it was confirmed that the E-cadherin and p53 proteins were not expressed in the primary tumor tissues formed in the Pdx1-Cre, Trp53$^{F/F}$, and Cdh1$^{F/F}$ mice.

EXAMPLE 2

Establishment of Primary Culture and Gastric Cancer Cell Line in the Murine-Derived Cancer Tissues In the present invention, the primary culturing was performed using the tumor tissues isolated in Example 1 for the establishment of a gastric cancer cell line.

Specifically, the tumor tissues observed in the stomach of the mouse model of Example 1 were cut off, washed with cold PBS, and the washed mass was transferred to a tissue culture dish containing a small amount of RPMI1640 medium, and the mass was minced into small slices using a surgical blade, and then prepared into smaller pieces via several pipetting. The thus-obtained minced mass was seeded into a 25 cm$^2$ flask containing RPMI1640 medium, which contained 20% FBS, 100 U/mL penicillin, and 0.1 mg/mL streptomycin. Upon observation of the formation of a sufficient amount of tumor cell population and the growth of heavy tumor cells, the first subculture was performed by trypsinization. After the first subculture, the subsequent subcultures were performed using RPMI1640 containing 10% FBS in 37° C., 5% $CO_2$ conditions (a total number of subcultures of 11 to 15).

As a result, the gastric cancer cell line deficient in E-cadherin and p53 was isolated and designated as NCC-S3. FIG. 2A shows the cell morphology of the NCC-S3 isolated from the above observed when they were cultured in a cell culture container, and it was observed that the NCC-S3 cell line showed the shape of epithelial cells.

EXAMPLE 3

Characterization of NCC-S3 Cell Line 3-1: Characterization Using Western Blot Analysis In the present invention, for characterizing the NCC-S3 cell line isolated in Example 2 and confirming whether the NCC-S3 cell line shows similarities to human gastric cancer cell line, the expression levels of pan-cytokeratin and proliferating cell nuclear antigen (PCNA) (FIG. 3A) and the expression levels of EGFR, p-Erk, p-Akt, Myc and cyclin D1 (FIG. 3B) were measured by western blot analysis.

First, for the isolation of proteins from the established gastric cancer cells, the cells were treated with the TPER reagent (Tissue Protein Extraction Reagent; Thermo Fisher Scientific, USA) added with a protease inhibitor (0.8 M aprotinin, 20 M leupeptin, 10 M pepstatin A, 40 M bestatin, and 1 mM phenylmethylsulfonyl fluoride (PMSF)) and a phosphatase inhibitor (1 mM sodium fluoride, 1 mM sodium pyrophosphate dehydrate, and 1 mM sodium orthovanadate).

The nuclear proteins of the murine-derived gastric cancer cell line were isolated according to the manual using a Qproteome nuclear protein extraction kit (Qiagen, USA), and the concentration of the isolated proteins was measured according to the BCA reagent kit (Thermo Fisher Scientific, USA).

The quantitated proteins were subjected to SDS-PAGE and western blot analysis according to the known methods (Park J W, et al., *Mol Cancer Res.*, 2014), and the primary antibodies used for the western blot analysis were those antibodies specific to pan-cytokeratin, PCNA, EGFR, p-Erk, p-Akt, Myc, and cyclin D1, and the respective antibodies for each of the proteins are as follows: mouse monoclonal anti pan-cytokeratin (1:1000; Santa Cruz, sc-8018), mouse monoclonal anti PCNA antibody (1:1000, Santa Cruz, sc-56), rabbit polyclonal anti c-Myc antibody (1:1000; Abcam, ab32072), rabbit polyclonal anti EGFR antibody (1:1000; Santa Cruz, sc-03), rabbit polyclonal anti p-Akt1/2/3 (Thr 308) antibody (1:1000, Santa Cruz, sc-16646-R), rabbit monoclonal anti Cyclin D1 antibody (1:1000, Cell Signaling, #2978S) and mouse monoclonal anti GAPDH antibody (1:1000, Santa Cruz, sc-32233).

Protein levels were measured by Fuji LAS-3000 system (Fujifilm, Japan) using the enhanced chemiluminescence (ECL) detection kit (Thermo Fisher Scientific Inc., USA), and the density of each band was measured using the ImageJ software (http://imagej.nih.gov/ij/), followed by normalization with GAPDH.

The normal cells (mouse conditionally immortalized stomach epithelial cells; ImSt), which were used as a control group, and the human gastric cancer cell line, i.e., AGS, were cultured in Royal Park Memorial Institute (RPMI) 1640 (Gibco, USA) containing 1% penicillin-streptomycin (Invitrogen, USA), and NIH-3T3, which is embryonic fibroblasts, was cultured in DMEN (Gibco, USA) containing 1% penicillin-streptomycin, and then the proteins were extracted therefrom using the following method and then subjected to western blot analysis.

As a result, as shown in FIGS. 3A and 3B, the AGS (the human gastric cancer cell line) and the NCC-S3 cell line (which was isolated in the present invention) have the same characteristics.

From these results, it can be speculated that the NCC-S3 cell line isolated in the present invention has an activated EGFR/MAPK signal and that Wnt/β-catenin signal is activated based on the overexpressed result of Myc and Cyclin D1, which are target molecules of Wnt.

Additionally, when the expression level of Myc was measured in the primary tumor tissues formed in the above cells in the same method as in Example 1-2, it was confirmed that the Myc overexpression was detected in the primary tumor.

3-2 : Characterization by Fluorescence Activated Cell Sorter (FACS)

The fluorescence activated cell sorter (FACS) analysis of CD44, CD133, and EpCAM in the NCC-S3 was performed using the FACSCalibur (BD Biosciences, USA) and analyzed according to the manual included therein.

First, the NCC-S3 cell line, which was cultured in Example 2, was treated with trypsin to separate the cells attached to the cell culture container, and the cells were stained by treating with rat anti-mouse CD133 PE (1:300; ebioscience, 12-1331-82), rat anti-mouse Epcam PE (1:200; ebioscience, 12-5791-82), rat anti-mouse CD44 FITC (1:200, ebioscience, 11-0441-82), rat IgG isotype control PE (BD pharminogen, 553930), and rat IgG isotype control FITC (ebioscience, 11-4031-81), respectively, and the staining reaction was performed in a dark room at 4° C. for 30 minutes while stirring gently.

The stained NCC-S3 cell line was resuspended in the FACS sorting buffer (1 mM EDTA, pH 7.0 25 mM HEPES, 1% FBS, and $Ca^{2+}$, $Mg^{2+}$ free PBS) and then analyzed using the FACSCalibur.

As a result, as shown in FIG. 5, the NCC-S3 cells were shown to overexpress CD44, CD133, and EpCAM, which are expressed in human gastric cancer. That is, the NCC-S3 cell line, which was established in the present invention, is very similar to that of human gastric cancer.

EXAMPLE 4

Establishment of a Gastric Cancer Cell Line with Improved Metastatic Capacity

In the present invention, the NCC-S3 cell line was transplanted subcutaneously into an SCID mouse for the establishment of a cell line with improved metastatic capacity, in addition to the NCC-S3 cell line.

Specifically, $1 \times 10^6$ NCC-S3 cells obtained in Example 2 were injected to the flank of a mouse with immune deficiency, and 115 days thereafter, the mouse was autopsied, and metastatic lesions were observed in the lung. The metastatic lesions were cut off and a cell line was established therefrom in the same method as in Example 2, and the cell line was designated as NCC-S3M.

FIG. 2B shows the cell morphology of the NCC-S3M isolated from the above observed when they were cultured in a cell culture container, and it was confirmed that the NCC-S3M cell line has the phenotype of epithelial mesenchymal transition (EMT).

EXAMPLE 5

Confirmation of Metastatic Property of NCC-S3M Cell Line

In the present invention, in order to confirm whether the gastric cancer cell line (NCC-S3M) newly obtained in Example 4 has the EMT phenotype compared to the parent cell (NCC-S3), the mRNA expression levels of Snail 1, Snail 2, Zeb 1, Zeb 2, Twist 1 and Twist 2, which are EMT activating transcription factors, were measured.

First, the total RNA was isolated from the murine-derived gastric cancer cell line using the AllPrep DNA/RNA/Protein Mini Kit (Qiagen, USA) according to the manual, and 0.3 μg of the thus-isolated total RNA was used to synthesize cDNA using the amfiRivertII reverse transcriptase (GenDEPOT, USA) referring to the manual provided in the kit.

PCR was performed using Roche LC480 (Roche Diagnostics, Germany) after adding 5 μL, of 2× QuantiTect SYBR Green PCR Master Mix (Qiagen), 400 nM of each primer, 2 μL of water, in which the cDNA was diluted at a 1:5 ratio, and water to a final volume of 10 μL, thereto.

Each of the primers used in the PCR was synthesized by requesting to Macrogen (www.macrogen.com/kor/), and the sequence information on each primer is shown in the following Table 1.

TABLE 1

Primer Sequences

| Name | Sequence (5' -> 3') | SEQ ID NO |
|---|---|---|
| Snail 1 Forward | 5'-CACACGCTGCCTTGTGTCT-3' | SEQ ID NO: 1 |
| Snail 1 Reverse | 5'-GGTCAGCAAAAGCACGGTT-3' | SEQ ID NO: 2 |
| Snail 2 Forward | 5'-CCTTGGGGCGTGTAAGTCC-3' | SEQ ID NO: 3 |
| Snail 2 Reverse | 5'-TTCTCAGCTTCGATGGCATGG-3' | SEQ ID NO: 4 |
| Zeb 1 Forward | 5'-TGATGAAAACGGAACACCAGATG-3' | SEQ ID NO: 5 |
| Zeb 1 Reverse | 5'-GTTGTCCTCGTTCTTCTCATGG-3' | SEQ ID NO: 6 |
| Zeb 2 Forward | 5'-AGCGACACGGCCATTATTTAC-3' | SEQ ID NO: 7 |
| Zeb 2 Reverse | 5'-GTTGGGCAAAAGCATCTGGAG-3' | SEQ ID NO: 8 |
| Twist 1 Forward | 5'-GGACAAGCTGAGCAAGATTCA-3' | SEQ ID NO: 9 |
| Twist 1 Reverse | 5'-CGGAGAAGGCGTAGCTGAG-3' | SEQ ID NO: 10 |
| Twist 2 Forward | 5'-ACGAGCGTCTCAGCTACGCC-3' | SEQ ID NO: 11 |
| Twist 2 Reverse | 5'-AGGTGGGTCCTGGCTTGCGG-3' | SEQ ID NO: 12 |
| GAPDH Forward | 5'-GGTCGGTGTGAACGGATTTG-3' | SEQ ID NO: 13 |
| GAPDH Reverse | 5'-GTGAGTGGAGTCATACTGGAAC-3' | SEQ ID NO: 14 |

A real-time PCR was performed in the following conditions: PCR was performed, after reacting at 95° C. for 15 minutes, for a total of 55 cycles, in which each cycle consisted of reacting at 94° C. for 20 seconds, 57° C. for 20 seconds, and at 72° C. for 20 seconds. The data was analyzed using the LC480 software (Roche Diagnostics).

The relative amount of mRNA expression was calculated using the ΔΔCT method, and the mRNA level of each gene was normalized using GAPDH.

As a result, as shown in FIG. 6, the NCC-S3M showed an increase in the mRNA levels of all of Snail 1, Snail 2, Zeb 1, Zeb 2, Twist 1 and Twist, compared to those of the NCC-S3, and the metastatic capacity of the NCC-S3M was shown to significantly increase compared to that of the NCC-S3.

EXAMPLE 6

Confirmation of Expression Levels of E-Cadherin and p53 in NCC-S3 and NCC-S3M Cell Lines In the present invention, in order to confirm whether the expression of E-cadherin and p53 were indeed deficient, western blot analysis was performed in the same method as in Example 3, and in addition, the expression amounts of Smad4 and vimentin were measured.

The primary antibodies for performing the western blot analysis are as follows: rabbit polyclonal anti E-cadherin antibody (1:1000; Cell Signaling, #3195), mouse monoclonal anti smad4 antibody (1:1000; Santa Cruz, sc-7966), rabbit polyclonal anti p53 antibody (1:1000; Santa Cruz, sc-6243), rabbit monoclonal anti vimentin antibody (1:1000; Cell signaling, #5741), and mouse monoclonal anti E-catenin antibody (1:1000; BD, 610154).

As a result, as shown in FIG. 7, it was observed that neither NCC-S3 nor NCC-S3M cell lines expressed E-cadherin and p53 and that vimentin was overexpressed only in the NCC-S3M cell line.

EXAMPLE 7

Confirmation of the Tumorigenic Capacity of NCC-S3 and NCC-S3M Cell Lines

For the confirmation of tumorigenic capacity and metastatic capacity of the two gastric cancer cell lines established in the present invention, heterotopic allografts of murine gastric cancer cells were formed.

First, $1\times10^6$ cells of each of the NCC-S3 and NCC-S3M cell lines were injected into the subcutaneous tissues on the flank of a severe combined immunodeficiency (SCID) mouse and a syngenic mouse. Then, the mice were autopsied when the tumor volume reached 2,500 mm³. The tumor volume (V) was calculated using the equation 1 below:

$$V = \tfrac{1}{2} \times a \times b^2 \qquad \text{[Equation 1]}$$

In the above equation, a and b indicate the longest diameter and the shortest diameter with each tumor mass, respectively.

TABLE 2

Frequency of pulmonary metastasis when the volume of heterotopic allografts reached 2,500 mm³ in an SCID mouse

| | Injection of Heterotopic | |
|---|---|---|
| | NCC-S3 | NCC-S3M |
| Frequency of pulmonary metastasis | 1/10 | 9/9 |

TABLE 3

Respective frequency upon confirmation of the presence of tumorigenesis (volume of 50 mm³ or greater) after 30 days of heterotopic injection into a syngenic mouse

| | Injection of Heterotopic | |
|---|---|---|
| | NCC-S3 | NCC-S3M |
| Presence of tumorigenesis | 3/10 | 9/10 |

As shown in FIG. 8, it was confirmed that the heterotopic allografts of the NCC-S3M grew faster than those of the NCC-S3 of an SCID mouse, and the heterotopic allografts of the NCC-S3M developed pulmonary metastasis in a concerted fashion when the volume of the primary tumor reached about 2,500 mm³. In addition, the NCC-S3M showed improved tumorigenic capacity compared to the NCC-S3.

On the contrary, only 10% developed metastasis in the heterotopic allografts of the NCC-S3, and this suggests that the NCC-S3M cells have improved tumorigenic capacity and metastatic capacity compared to the NCC-S3 cells.

EXAMPLE 8

Confirmation of Wnt/β-Catenin Signaling Activity of NCC-S3 and NCC-S3M Cell Lines In the present invention, in order to confirm whether Wnt/β-catenin signal is activated indeed in the NCC-S3 and NCC-S3M cell lines isolated in the present invention, the expression levels of TCF/LEF1 and β-catenin, the mRNA expression levels of Mmp3 and Mmp14, and Mmp3 and Mmp14, and the mRNA expression levels of Wnt5a, Wnt10b and Fzd8 were measured.

8-1: Measurement of the Activity of TCF/LEF1 Reporter

The activity of β-catenin was measured via TCF/LEF1 reporter assay method, and TCF/LEF1 is known to act as a transcription factor which binds to DNA during the Wnt/β-catenin signaling process.

The activity of β-catenin was measured using the TCF/LEF1 reporter assay kit (CCS-018L, SA Biosciences, USA). First, NCC-S3 and NCC-S3M cell lines were suspended in 1 mL of Opti-MEM medium (Life Technologies, USA) to have 2×10⁵ cells, respectively, and then seeded into a 12-well plate.

The seeded cells were transiently transfected by mixing with a Tcf/Lef reporter plasmid using the Lipofectamine 2000 transfection reagent. Twenty four hours after the transfection, the Opti-MEM medium was replaced with RPMI 1640 containing 0.5% FBS and cultured for 48 hours thereafter.

Luciferase assays were performed using a dual luciferase reporter assay system (Promega, USA) according to the manual. The light emission was quantitated using the Victor 3 1420 luminescence microplate reader (Perkin-Elmer, USA), and with respect to the signal, the transfection efficiency was normalized using the internal Renilla control group.

As a result, as shown in FIG. 9, the activity of the TCF/LEF1 was shown to increase in the NCC-S3M cell line, and it was confirmed that the activity of the NCC-S3M cell line was increased compared to the NCC-S3 cell line, which is the parental cell of the NCC-S3M cells.

8-2: Measurement of the Expression Amount of β-Catenin Protein

The expression amount of β-catenin protein was measured by western blot analysis in the same method as in Example 3, and mouse monoclonal anti β-catenin antibodies (1:1000; BD, 610154) were used as the primary antibodies for performing the western blot analysis.

As shown in FIG. 10, it was confirmed that the NCC-S3M showed a higher level of β-catenin expression in the nucleus compared to the NCC-S3.

8-3: Confirmation of mRNA Expression of Mmp3 and Mmp14

In the present invention, the mRNA expression levels of Mmp3 and Mmp14, which are known as target genes of β-catenin, were measured in the same method as in Example 5, and each of the primers used in the PCR was synthesized by requesting to Macrogen (www.macrogen.com/kor/), and the sequence information on each primer is shown in the following Table 4.

TABLE 4

Primer Sequences

| Name | | Sequence (5' -> 3') | SEQ ID NO |
|---|---|---|---|
| Mmp3 | Forward | 5'-GCAGTTGGAGAACATGGAGAC-3' | SEQ ID NO: 15 |
| | Reverse | 5'-AATAGGTTGGTACCAGTGACATCC-3' | SEQ ID NO: 16 |
| Mmp14 | Forward | 5'-CTTCAAGGAGCGATGGTTCTG-3' | SEQ ID NO: 17 |
| | Reverse | 5'-TTGCCATCCTTCCTCTCGTAG-3' | SEQ ID NO: 18 |

As a result, as shown in FIG. 11, the mRNA expression levels of Mmp3 and Mmp14 in the NCC-S3M cell line measured were 10-fold and 3-fold higher than those of the NCC-S3 cell line, respectively. That is, the mRNAs of Mmp3 and Mmp14 were overexpressed in the NCC-S3M cell line, according to the activation of β-catenin signal.

8-4: Confirmation of Wnt Signal

In the present invention, in order to confirm whether Wnt signal was activated in the NCC-S3 and NCC-S3M cell lines, the mRNA expression levels of Wnt5a, Wnt10b, and Fzd8 (frizzled-8) were measured in the same method as in Example 5, and each of the primers used in the PCR was synthesized by requesting to Macrogen (www.macrogen.com/kor/), and the sequence information on each primer is shown in the following Table 5.

TABLE 5

Primer Sequences

| Name | | Sequence (5' -> 3') | SEQ ID NO |
|---|---|---|---|
| Wnt5a | Forward | 5'-GCAGGCCGTAGGACAGTATA-3' | SEQ ID NO: 19 |
| | Reverse | 5'-CCGCGCTATCATACTTCTCC-3' | SEQ ID NO: 20 |
| Wnt10b | Forward | 5'-CTCAAGCGCGGTTTCCGTGA-3' | SEQ ID NO: 21 |
| | Reverse | 5'-CTAAGCCGGTCTTGCTCACC-3' | SEQ ID NO: 22 |
| Fzd8 | Forward | 5'-ACTCGCAGTACTTCCACCTG-3' | SEQ ID NO: 23 |
| | Reverse | 5'-GGTTGTCAAGGCTCTGGTTG-3' | SEQ ID NO: 24 |

As shown in FIG. 12, the mRNA expression levels of Wnt5a, Wnt10b, and Fzd8 (frizzled-8) in the NCC-S3M cell line were increased a 3-fold, a 10.5-fold, and a 5-fold, respectively, compared to those of the NCC-S3 cell line.

That is, it was confirmed that the Wnt/β-catenin signaling process was indeed activated in the NCC-S3M cell line, which was established in the present invention, and this suggests that the metastatic phenotype of the NCC-S3M cell line, which is a metastatic cell line, may be partially resulted from EMT through the activation of the β-catenin signaling pathway.

The present inventors have established the NCC-S3 and NCC-S3M cell lines, i.e., murine-derived gastric cancer cell lines, which closely mimic the human gastric cancer and are useful for the experiments for testing immunotherapeutic agents, and deposited these cell lines to the Korean Cell Line Bank on Jul. 10, 2014 (the NCC-S3 cell line: Korean Cell Line Bank Accession No. KCLRF-BP-00320, and the NCC-S3M cell line: Korean Cell Line Bank Accession No. KCLRF-BP-00321).

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

[Deposition No.]
Depositary Authority: Korean Cell Line Bank
Accession No.: KCLRFBP00320
Date of Deposition: 20140710
Depositary Authority: Korean Cell Line Bank
Accession No.: KCLRFBP00321
Date of Deposition: 20140710

What is claimed is:

1. A gastric cancer cell line deficient in E-cadherin and p53, wherein the gastric cancer cell line is Korean Cell Line Bank Accession No. KCLRF-BP-00320 or Korean Cell Line Bank Accession No. KCLRF-BP-00321.

2. The gastric cancer cell line of claim 1, wherein the gastric cancer cell line is derived from a mouse.

3. The gastric cancer cell line of claim 1, wherein the gastric cancer cell line is isolated from gastric adenocarcinoma naturally formed in Pdx1-cre, Trp53$^{F/F}$, and Cdh1$^{F/F}$ mice.

4. The gastric cancer cell line of claim 1, wherein the gastric cancer cell line with Accession No. KCLRF-BP-00321 is isolated from a pulmonary metastasis product of heterotopic allografts of the gastric cancer cell line with Accession No. KCLRF-BP-00320.

5. The gastric cancer cell line of claim 1, wherein the gastric cancer cell line with Accession No. KCLRF-BP-00321 has a phenotype of epithelial mesenchymal transition (EMT), overexpressed vimentin, and an activated Wnt/β-catenin pathway.

6. A method for evaluating efficacy of one or more candidate therapeutic agents for treating gastric cancer, comprising:
(a) treating a cell of at least one gastric cancer cell line, the gastric cancer cell line being selected from the group consisting of Korean Cell Line Bank Accession No. KCLRF-BP-00320 and Korean Cell Line Bank Accession No. KCLRF-BP-00321, with at least one candidate agent that is selected from a candidate therapeutic agent for treating gastric cancer and a candidate metastasis inhibitor of gastric cancer; and
(b) measuring either or both of (i) a level of inhibition of growth or proliferation of the gastric cancer cell line cell of step (a) and (ii) a level of inhibition of metastasis of the gastric cancer cell line cell of step (a).

* * * * *

SEQUENCE LISTING

```
<160> NUMBER OF SEQ ID NOS: 24

<210> SEQ ID NO 1
<211> LENGTH: 19
<212> TYPE: DNA
<213> ORGANISM: Artificial
<220> FEATURE:
<223> OTHER INFORMATION: Snail 1 Forward primer

<400> SEQUENCE: 1
cacacgctgc cttgtgtct                                                 19

<210> SEQ ID NO 2
<211> LENGTH: 19
<212> TYPE: DNA
<213> ORGANISM: Artificial
<220> FEATURE:
<223> OTHER INFORMATION: Snail 1 Reverse primer

<400> SEQUENCE: 2
ggtcagcaaa agcacggtt                                                 19

<210> SEQ ID NO 3
<211> LENGTH: 19
<212> TYPE: DNA
<213> ORGANISM: Artificial
<220> FEATURE:
<223> OTHER INFORMATION: Snail 2 Forward primer

<400> SEQUENCE: 3
ccttggggcg tgtaagtcc                                                 19
```

```
<210> SEQ ID NO 4
<211> LENGTH: 21
<212> TYPE: DNA
<213> ORGANISM: Artificial
<220> FEATURE:
<223> OTHER INFORMATION: Snail 2 Reverse primer

<400> SEQUENCE: 4
ttctcagctt cgatggcatg g                                              21

<210> SEQ ID NO 5
<211> LENGTH: 23
<212> TYPE: DNA
<213> ORGANISM: Artificial
<220> FEATURE:
<223> OTHER INFORMATION: Zeb 1 Forward primer

<400> SEQUENCE: 5
tgatgaaaac ggaacaccag atg                                            23

<210> SEQ ID NO 6
<211> LENGTH: 22
<212> TYPE: DNA
<213> ORGANISM: Artificial
<220> FEATURE:
<223> OTHER INFORMATION: Zeb 1 Reverse primer

<400> SEQUENCE: 6
gttgtcctcg ttcttctcat gg                                             22

<210> SEQ ID NO 7
<211> LENGTH: 21
<212> TYPE: DNA
<213> ORGANISM: Artificial
<220> FEATURE:
<223> OTHER INFORMATION: Zeb 2 Forward primer

<400> SEQUENCE: 7
agcgacacgg ccattattta c                                              21

<210> SEQ ID NO 8
<211> LENGTH: 21
<212> TYPE: DNA
<213> ORGANISM: Artificial
<220> FEATURE:
<223> OTHER INFORMATION: Zeb 2 Reverse primer

<400> SEQUENCE: 8
gttgggcaaa agcatctgga g                                              21

<210> SEQ ID NO 9
<211> LENGTH: 21
<212> TYPE: DNA
<213> ORGANISM: Artificial
<220> FEATURE:
<223> OTHER INFORMATION: Twist 1 Forward primer

<400> SEQUENCE: 9
ggacaagctg agcaagattc a                                              21

<210> SEQ ID NO 10
<211> LENGTH: 19
<212> TYPE: DNA
<213> ORGANISM: Artificial
<220> FEATURE:
<223> OTHER INFORMATION: Twist 1 Reverse primer
```

```
<400> SEQUENCE: 10
cggagaaggc gtagctgag                                                19

<210> SEQ ID NO 11
<211> LENGTH: 20
<212> TYPE: DNA
<213> ORGANISM: Artificial
<220> FEATURE:
<223> OTHER INFORMATION: Twist 2 Forward primer

<400> SEQUENCE: 11
acgagcgtct cagctacgcc                                               20

<210> SEQ ID NO 12
<211> LENGTH: 20
<212> TYPE: DNA
<213> ORGANISM: Artificial
<220> FEATURE:
<223> OTHER INFORMATION: Twist 2 Reverse primer

<400> SEQUENCE: 12
aggtgggtcc tggcttgcgg                                               20

<210> SEQ ID NO 13
<211> LENGTH: 20
<212> TYPE: DNA
<213> ORGANISM: Artificial
<220> FEATURE:
<223> OTHER INFORMATION: GAPDH Forward primer

<400> SEQUENCE: 13
ggtcggtgtg aacggatttg                                               20

<210> SEQ ID NO 14
<211> LENGTH: 22
<212> TYPE: DNA
<213> ORGANISM: Artificial
<220> FEATURE:
<223> OTHER INFORMATION: GAPDH Reverse primer

<400> SEQUENCE: 14
gtgagtggag tcatactgga ac                                            22

<210> SEQ ID NO 15
<211> LENGTH: 21
<212> TYPE: DNA
<213> ORGANISM: Artificial
<220> FEATURE:
<223> OTHER INFORMATION: Mmp3 Forward primer

<400> SEQUENCE: 15
gcagttggag aacatggaga c                                             21

<210> SEQ ID NO 16
<211> LENGTH: 24
<212> TYPE: DNA
<213> ORGANISM: Artificial
<220> FEATURE:
<223> OTHER INFORMATION: Mmp3 Reverse primer

<400> SEQUENCE: 16
aataggttgg taccagtgac atcc                                          24

<210> SEQ ID NO 17
```

```
<211> LENGTH: 21
<212> TYPE: DNA
<213> ORGANISM: Artificial
<220> FEATURE:
<223> OTHER INFORMATION: Mmp14 Forward primer

<400> SEQUENCE: 17
cttcaaggag cgatggttct g                                              21

<210> SEQ ID NO 18
<211> LENGTH: 21
<212> TYPE: DNA
<213> ORGANISM: Artificial
<220> FEATURE:
<223> OTHER INFORMATION: Mmp14 Reverse primer

<400> SEQUENCE: 18
ttgccatcct tcctctcgta g                                              21

<210> SEQ ID NO 19
<211> LENGTH: 20
<212> TYPE: DNA
<213> ORGANISM: Artificial
<220> FEATURE:
<223> OTHER INFORMATION: Wnt5a Forward primer

<400> SEQUENCE: 19
gcaggccgta ggacagtata                                                20

<210> SEQ ID NO 20
<211> LENGTH: 20
<212> TYPE: DNA
<213> ORGANISM: Artificial
<220> FEATURE:
<223> OTHER INFORMATION: Wnt5a Reverse primer

<400> SEQUENCE: 20
ccgcgctatc atacttctcc                                                20

<210> SEQ ID NO 21
<211> LENGTH: 20
<212> TYPE: DNA
<213> ORGANISM: Artificial
<220> FEATURE:
<223> OTHER INFORMATION: Wnt10b Forward primer

<400> SEQUENCE: 21
ctcaagcgcg gtttccgtga                                                20

<210> SEQ ID NO 22
<211> LENGTH: 20
<212> TYPE: DNA
<213> ORGANISM: Artificial
<220> FEATURE:
<223> OTHER INFORMATION: Wnt10b Reverse primer

<400> SEQUENCE: 22
ctaagccggt cttgctcacc                                                20

<210> SEQ ID NO 23
<211> LENGTH: 20
<212> TYPE: DNA
<213> ORGANISM: Artificial
<220> FEATURE:
<223> OTHER INFORMATION: Fzd8 Forward primer

<400> SEQUENCE: 23
```

```
actcgcagta cttccacctg                                               20

<210> SEQ ID NO 24
<211> LENGTH: 20
<212> TYPE: DNA
<213> ORGANISM: Artificial
<220> FEATURE:
<223> OTHER INFORMATION: Fzd8 Reverse primer

<400> SEQUENCE: 24
ggttgtcaag gctctggttg                                               20
```